United States Patent [19]

Worthington

[11] 4,416,682
[45] Nov. 22, 1983

[54] 1,3-BIS(AZOLYL)PROPANOLS AS FUNGICIDES AND PLANT GROWTH REGULATORS

[75] Inventor: Paul A. Worthington, Maidenhead, England

[73] Assignee: Imperial Chemical Industries PLC, London, England

[21] Appl. No.: 269,581

[22] Filed: Jun. 2, 1981

[30] Foreign Application Priority Data

Jun. 2, 1980 [GB] United Kingdom ............... 8017959
Mar. 30, 1981 [GB] United Kingdom ............... 8109923

[51] Int. Cl.³ .................... A01N 43/50; A01N 43/64; C07D 233/61; C07D 249/08
[52] U.S. Cl. .......................... 71/76; 71/92; 424/245; 424/269; 424/273 R; 548/101; 548/262; 548/336; 548/341; 568/807; 568/809; 568/812; 568/844
[58] Field of Search ............ 548/262, 101, 336; 424/245, 269, 273 R; 71/76, 92

[56] References Cited

U.S. PATENT DOCUMENTS 4,079,143 3/1978 Balasubramanyan et al. ..... 548/262
4,301,166 11/1981 Regel et al. ...................... 568/337

FOREIGN PATENT DOCUMENTS 2654890 6/1977 Fed. Rep. of Germany ...... 548/262
2908378 9/1980 Fed. Rep. of Germany ...... 548/262

*Primary Examiner*—Alton D. Rollins
*Attorney, Agent, or Firm*—Cushman, Darby & Cushman

[57] ABSTRACT

Fungicidal compounds of the formula:

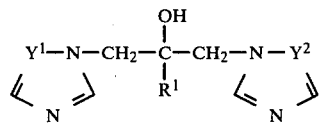

wherein $R^1$ is an optionally substituted-alkyl, -cycloalkyl, -aryl or -aralkyl group, $Y^1$ and $Y^2$ are $=CH-$ or $=N-$; and salts, metal complexes, ethers and esters thereof.

7 Claims, No Drawings

1,3-BIS(AZOLYL)PROPANOLS AS FUNGICIDES AND PLANT GROWTH REGULATORS

This invention relates to triazole and imidazole compounds useful as fungicides, to a process for preparing them, to fungicidal and plant growth regulating compositions containing them, to processes using them to combat fungal infections in plants, and to regulate plant growth. The invention also relates to pharmaceutical and veterinary compositions comprising triazole and imidazole compounds, and in particular to such compositions which are orally or topically active against fungus diseases of humans and other animals. These compositions of the invention are especially useful for treatment of candidiasis and human dermatophyte infections.

The invention provides a compound having the formula (I):

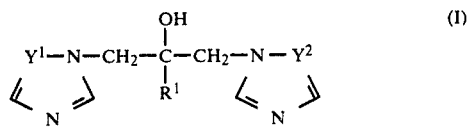

wherein $R^1$ is an optionally substituted-alkyl, -cycloalkyl (e.g. cyclopentyl or cyclohexyl), -aryl (e.g. phenyl) or -aralkyl (e.g. benzyl) group; and $Y^1$ and $Y^2$ are =CH— or =N—; and salts or metal complexes, ethers and esters thereof.

The invention further provides a compound having the formula:

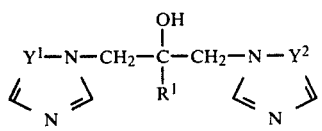

wherein $R^1$ is alkyl, cycloalkyl, optionally substituted aryl or optionally substituted aralkyl; and $Y^1$ and $Y^2$ are either both =CH— or both =N—; or an acid addition salt or metal complex thereof.

The compounds of the invention can contain chiral centres. Such compounds are generally obtained in the form of racemic mixtures. However, these and other mixtures can be separated into the individual isomers by methods known in the art.

The alkyl groups can be a straight or branched chain group having 1 to 6, e.g. 1 to 4, carbon atoms; examples are methyl, ethyl, propyl (n- or iso-propyl) and butyl (n-, sec-, iso- or t-butyl). These alkyl groups can be optionally substituted, for example with halogen atoms or alkoxy groups, or any suitable substituent defined below.

Examples of suitable substituents for the aryl and for the aryl moiety of the aralkyl are halogen (e.g. fluorine, chlorine or bromine), $C_{1-5}$ alkyl or haloalkyl [e.g. methyl, ethyl, propyl (n- or iso-propyl), butyl (n-, sec-, iso- or t-butyl) or trifluoromethyl]; alkenyl (e.g. vinyl), $C_{1-4}$ alkoxy (e.g. methoxy and ethoxy) or haloalkoxy, nitro, cyano, hydroxy, alkylthio containing from 1 to 4 carbon atoms, phenyl and phenoxy. The alkyl moiety of the benzyl can be substituted with for example alkyl or aryl (e.g. methyl, ethyl or phenyl). The foregoing substituents may themselves bear substituents as already defined. For example a phenyl substituent may itself bear one or more substituent groups such as halogen, alkoxy, alkyl, nitro, haloalkyl, haloalkoxy or hydroxy. Suitably the aryl and aralkyl are unsubstituted or substituted with 1, 2 or 3 ring substituents as defined above. Preferably the benzyl and phenyl have one, two or three ring substituents, and preferably one or two substituents in the o-position and/or p-positions. Examples of these groups are phenyl, benzyl, α-methylsubstituted benzyl, o-, m- or p-chlorophenyl, 2,4- or 2,6-dichlorophenyl, o, m- or p-fluorophenyl, 2,6-difluorophenyl, o-, m- or p-bromophenyl, 2-chloro-4-fluorophenyl, 2-chloro-6-fluorophenyl, o-, m- or p-methoxyphenyl, 2,4-dimethoxyphenyl, o-, m- or p-ethoxyphenyl, o-, m- or p-nitrophenyl, o-, m- or p-methylphenyl, o-, m- or p-t-butylphenyl, o-, m- or p-trifluoromethylphenyl, o-, m- or p-phenoxyphenyl, and o-, m- or p-phenylphenyl (o-, m- or p-biphenyl), and the corresponding ring substituted benzyl and α-methyl-benzyl groups.

The present invention further provides a compound according to formula I above wherein $R^1$ is either an alkyl group containing from 1 to 6 carbon atoms, optionally halo- or alkoxy-substituted, or is cyclopentyl or cyclohexyl, either optionally halo- or alkoxy-substituted. $C_{1-4}$ alkoxy groups are preferred.

The present invention, more particularly, provides a compound according to formula I above wherein $R^1$ is phenyl or benzyl, both of which may be optionally substituted with one or more of the following: halogen, alkyl or haloalkyl each containing from 1 to 5 carbon atoms, alkoxy or haloalkoxy each containing from 1 to 4 carbon atoms, nitro, cyano, hydroxy, alkylthio containing from 1 to 4 carbon atoms, or phenyl or phenoxy groups both optionally substituted; and wherein the alkyl moiety of the benzyl is optionally substituted with alkyl containing from 1 to 4 carbon atoms or aryl.

The present invention especially provides a compound wherein $R^1$ is phenyl or benzyl, each unsubstituted, or substituted with one, two or three of the following: halogen, methyl, methoxy, trifluoromethyl, trifluoromethoxy, phenyl, halophenyl, phenoxy, or vinyl groups; and wherein the alkyl moiety of the benzyl is optionally substituted with methyl, ethyl or phenyl.

The ethers of the alcohols can be alkyl, alkenyl, alkynyl, aryl or aralkyl ethers, for example methyl, ethyl, propyl, butyl, phenyl, benzyl, p-chlorobenzyl, allyl or propargyl. The esters of the alcohols can be alkanoyl, benzoyl or sulphonyl esters, for example acetate, pivaloate, benzoate, tosylate or mesylate esters.

The salts can be salts with inorganic or organic acids e.g. hydrochloric, nitric, sulphuric, acetic, p-toluenesulphonic or oxalic acid. The salts may also be quaternary salts.

Suitably the metal complex is one including, as the metal, copper, zinc, manganese or iron.

The present invention further provides fungicidal, and plant growth regulating compositions comprising, as an active ingredient, a compound of formula (I) as defined above or a salt, metal complex, ether or ester thereof. These compositions may contain a carrier substance for the active ingredient.

The present invention further provides a pharmaceutical or veterinary fungicidal composition which comprises a compound of formula I as defined above, or a salt, metal complex, ether or ester thereof, together with a pharmaceutically or veterinary acceptable diluent or carrier.

Examples of the compounds of the inventon are shown in Table I.

nol, acetonitrile, or dimethylformamide, at a temperature of 20°–100° C. Preferably the dihalopropan-2-ol is added to an excess of the sodium salt of the heterocyclic base in dimethylformamide at 100° C. The product can be isolated by adding the solution to water followed by recrystallisation.

The 1,3-dihalopropan-2-ols can be made by reacting a 1,3-dihaloacetone with the appropriate Grigard reagent according to known methods (e.g. Johnson et al, J. Org. Chem., 1962, 27, 2241–3).

The compounds (I) of the invention may also be made by reacting a compound of general formula (III)

TABLE I

| COMPOUND | $R^1$ | $Y^1$ | $Y^2$ | Melting Point (°C.) |
|---|---|---|---|---|
| 1 | 4-Cl—$C_6H_4$— | =N— | =N— | 153–155° |
| 2 | $C_6H_5$— | =N— | =N— | 99–101° |
| 3 | 4-F—$C_6H_4$— | =N— | =N— | 124–126° |
| 4 | 2,4-diCl—$C_6H_3$ | =N— | =N— | 183–186° |
| 5 | 2,4-diCl—$C_6H_3$—$CH_2$— | =N— | =N— | 137–140° |
| 6 | 4-$CH_3$—$C_6H_4$— | =N— | =N— | 179–180° |
| 7 | 4-$C_6H_5$—$C_6H_4$— | =N— | =N— | 165–170° |
| 8 | 4-$CH_3O$—$C_6H_4$— | =N— | =N— | 141–143° |
| 9 | 2-Cl—$C_6H_4$— | =N— | =N— | 145–148° |
| 10 | 4-$C_6H_5O$—$C_6H_4$— | =N— | =N— | 163–165° |
| 11 | 2-$CF_3$—$C_6H_4$— | =N— | =N— | |
| 12 | 2,4-diCl—$C_6H_3$— | =CH— | =CH— | 160–175° |
| 13 | 2,4-diCl—$C_6H_3$— | =N— | —CH— | 169–170° |
| 14 | n-$C_4H_9$— | =N— | =N— | 61–62° |
| 15 | 4-Cl—$C_6H_4CH_2$— | =N— | =N— | |
| 16 | 2-Cl—$C_6H_4CH_2$— | =N— | =N— | |
| 17 | 2,6-diCl—$C_6H_3CH_2$— | =N— | =N— | |
| 18 | 4-$CH_3O$—$C_6H_4CH_2$— | =N— | =N— | |
| 19 | $C_6H_5CH_2$— | =N— | =N— | |
| 20 | 2,4-diCl$C_6H_3$CH— <br>             \|<br>            $CH_3$ | =N— | =N— | |
| 21 | 4-Cl—$C_6H_4$CH—<br>            \|<br>            $C_6H_5$ | =N— | =N— | |
| 22 | 4-Cl—$C_6H_4$—CH—<br>                \|<br>          4-Cl—$C_6H_4$ | =N— | =N— | |
| 23 | 2,6-diCl$C_6H_3$— | =N— | =N— | |
| 24 | 4-$CF_3OC_6H_4$— | =N— | =N— | |
| 25 | 2,4,6-triCl$C_6H_2$— | =N— | =N— | |
| 26 | 4-(Cl—$C_6H_4$)$C_6H_4$— | =N— | =N— | |
| 27 | 2-($C_6H_5O$)$C_6H_4$— | =N— | =N— | |
| 28 | 4-$CH_2$=CH—$C_6H_4$— | =N— | =N— | |
| 29 | t-$C_4H_9$— | =N— | =N— | |
| 30 | i-$C_4H_9$— | =N— | =N— | |
| 31 |  | =N— | =N— | |
| 32 | t-$C_4H_9CH_2$ | =N— | =N— | |
| 33 | 3,4-diCl$C_6H_3$— | =N— | =N— | 140–145° aq. ethanol/water 1:9 |

In the above Table the following is a key to the abbreviations used
t- = tertiary
i- = iso

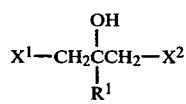 = cyclohexyl diCl = dichloro-
triCl = trichloro-

The compounds of general formula (I) above may be prepared by reacting a 1,3-dihalo-propan-2-ol of general formula (II)

$$X^1-CH_2\underset{\underset{R^1}{|}}{\overset{\overset{OH}{|}}{C}}CH_2-X^2 \qquad (II)$$

where each of $X^1$ and $X^2$, which may be the same or different, is halogen (chlorine or bromine), and $R^1$ is as defined above, with imidazole or 1,2,4-triazole or a salt thereof (e.g. the sodium salt). This reaction can be performed in a convenient solvent such as methanol, etha-

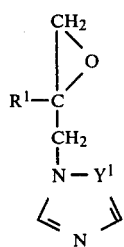  (III)

wherein R¹ and Y¹ are as defined above, with imidazole or 1,2,4-triazole or a salt thereof (e.g. the sodium salt) in a convenient solvent by the method outlined above.

The epoxides of general formula (III) may be prepared by reacting a ketone (IV)

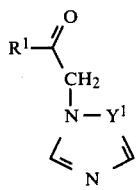  (IV)

where R¹ and Y¹ are defined above, with dimethyl oxosulphonium methylide (Corey and Chaykovsky, JACS, 1965, 87, 1353-1364) or dimethyl sulphonium methylide (Corey and Chaykovsky, JACS, 84, 3782) using methods set out in the literature.

Compounds (IV) can be made by methods set out in the patent literature, more particularly in British Patent Specification Nos. 1533705 and 1533706, which are herein incorporated by reference.

In an alternative procedure the compounds of the invention can be prepared by reacting a compound of general formula (V)

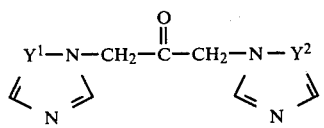  (V)

where Y¹ and Y² are as defined above with a Grignard reagent (VI)

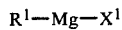  (VI)

where R¹ and X¹ are defined by methods set out in the literature (e.g. Johnson et al, J.Org.Chem., 1962, 27, 2241-3).

The compounds of general formula (V) can be prepared by reacting a 1,3-dihaloacetone with imidazole or 1,2,4-triazole or a salt thereof (e.g. the sodium salt) in a convenient solvent by the method previously described.

The salts and metal complexes of the compounds of general formula (I) can be prepared from the latter in known manner. For example, the complexes can be made by reacting the uncomplexed compound with a metal salt in a suitable solvent.

The ethers are made by treating the sodium salt of the alcohol with a reactive halogenated compound (e.g. methyl bromide or iodide, benzyl chloride, or allyl bromide). The esters are made in a similar manner by treating the sodium salt of the alcohol with an acid chloride (e.g. acetyl chloride, benzoyl chloride or methane sulphonyl chloride).

The compounds and salts, metal complexes, ethers and esters thereof, are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines ;P0 Helminthosporium spp. and Rhynchosporium spp. on cereals

*Cercospora arachidicola* on peanuts and other Cercospora species on for example suggar beet, bananas and soya beans *Botrytis cinerea* (grey mould) on tomatoes, strawberries, vines and other hosts

*Phytophthora infestans* (late blight) on tomatoes

*Venturia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: Fusarium spp., Septoria spp., Tilletia spp. (i.e. bunt, a seed borne disease of wheat), Ustilago spp., Helminthosporium spp. on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

The compounds, and their derivatives as defined above, also have plant growth regulating activities.

The plant growth regulating effects of the compounds are manifested as for example a stunting or dwarfing effect on the vegetative growth of woody and herbaceous mono- and di-cotyledonous plants. Such stunting or dwarfing may be useful, for example, in peanuts, cereals and soya bean where reduction in stem growth may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata,* Festuca spp. (e.g. *Festuca rubra*) and Poa spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect of flower head emergence in for example grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturising ornamental, household, garden and nursery plants (e.g. poinsettias, chrysanthemums, carnations, tulips and daffodils).

As indicated above, the compounds can also be used to stunt woody species. This property can be used to control hedgerows or to shape fruit trees (e.g. apples). Some coniferous trees are not significantly stunted by the compounds so the compounds could be useful in controlling undesirable vegetation in conifer nurseries.

The plant growth regulating effect may (as implied) above) manifest itself in an increase in crop yield.

In the potato, vine control in the field and inhibition of sprouting in the store may be possible.

Other plant growth regulating effects caused by the compounds include alteration of leaf angle and promotion of tillering in monocotyledonous plants. The former effect may be useful for example in altering the leaf orientation of, for example, potato crops thereby letting more light into the crops and including an increase in phytosynthesis and tuber weight. By increasing tillering in monocotyledonous crops (e.g. rice), the number of flowering shoots per unit area may be increased thereby increasing the overall grain yield of such crops. In grass swards an increase in tillering could lead to a denser sward which may result in increased resilience in wear.

The treatment of plants with the compounds can lead to the leaves developing a darker green colour.

The compounds may inhibit, or at least delay, the flowering of sugar beet and thereby may increase sugar yield. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus further provides a fungicidal or plant growth regulating composition comprising a compound of general formula (I) as hereinbefore defined, or a salt, metal complex, ether or ester thereof; and, optionally, a carrier or diluent.

The invention also provides a method of combating fungi, which comprises applying to a plant, to seed of a plant or to the locus of a plant or seed, a compound, or salt, metal complex, ether or ester thereof, as hereinbefore defined.

The invention also provides a method of regulating plant growth which comprises applying to a plant, to seed of a plant or to the locus of a plant or seed, a compound, or salt, metal complex, ether or ester thereof, as hereinbefore defined.

The compounds, salts, metal complexes, ethers and esters can be applied in a number of ways, for example they can be formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour. Application can be to any part of the plant, bush or tree, for example to the foilage, stems, branches or roots, or to soil surrounding the roots, or to the seed before it is planted.

The term "plant" as used herein includes seedlings, bushes and trees. Furthermore, the fungicidal method of the invention includes preventive, protectant, prophylactic and eradicant treatment.

The compounds are preferably used for agricultural and horitcultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and puspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g., 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt, metal complex, ether or ester complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-anionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzene-sulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogenous for a sufficient time to enable them to be applied by conventional spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylene-sulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal or plant growth regulating activity or compounds having herbicidal or insecticidal activity.

The other fungicidal compound can be for example one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim (BCM), thiophanate-methyl, captafol, captan, sulphur, dithiocarbamates, carbathiins, copper oxychloride, triforine, dodemorph, tridemorph, dithianon, pyrazophos, binapacryl, quinomethionate, panoctine, furalaxyl, aluminium tris(ethylphosphonate), DPX3217, ethirimol, dimethirimol, bupirimate, chlorothalonil and metaxanine.

Suitable insecticides are pirimor, croneton, dimethoate, metasystox and formothion.

The other plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or flower as a plant growth regulating agent. Some of these other agents will be herbicides. Examples of suitable agents are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g., kinetin, diphenylurea, benzimidazole, benzyladenine or BAP), phenoxyacetic acids (e.g. 2,4-D or MCPA), substituted benzoic acids (e.g. TIBA), morphactins (e.g. chlorfluorecol), maleic hydrazide, glyphosate, glyphosine, long chain fatty alcohols and acids (e.g. Off Shoot 0 or Off Shoot T), dikegulac, Sustar, Embark, substituted quaternary ammonium and phosphonium compounds (e.g. CCC or Phosfon-D), Ethrel, carbetamide, Racuza, Alar, asulam, abscissic acid, isopyrimil, RH531, hydroxybenzonitriles, (e.g. bromoxynil), Avenge, Suffix or Lontrel.

The pharmaceutical and veterinary compositions of the invention may be in a conventional pharmaceutical form suitable for oral administration, for example a tablet, a capsule, an emulsion or an aqueous or oily solution or suspension, or suitable for topical application, for example a cream, ointment or gel. The composition may contain conventional phamaceutical excipients, and may be manufactured by conventional pharmaceutical techniques.

Preferred pharmaceutical or veterinary compositions of the invention are compositions suitable for oral administration, and particularly tablets and capsules.

The antifungal activity of the active ingredients of the compositions of the invention against *Candida albicans,* a causative fungus of candidiasis, and *Trichophyton mentagrophytes,* var. *quinkeanum,* was demonstrated as follows:

Female mice of around 30 g weight are injected subcutaneously on a Friday with 0.5 mg of oestradiol benzoate. The following Monday (day 0) they are clipped on the back and then dosed orally with test compounds. They are then inoculated with *Candida albicans* in the vagina and *Trichophyton mentagrophytes* var. *quinkeanum* on the back, and then given a second dose of the same compound. Dosing is repeated once daily on days 1 to 4. On day 7 skin lesions are scored visually and vaginal samples taken for culture on agar. Groups of 5 mice are used and compounds are dosed initially at a level of 250 mg/kg. The dose is then reduced sequentially until a minimum effective dose (MED) is found. In this test compound 4 of Table I was active against Candida at a level of 1 mg/kg (milligrams per kilogram).

The following Examples illustrate the invention; the temperatures are given in degrees Centigrade (°C).

EXAMPLE 1

This Example illustrates the preparation of the compound 1,3-Bis-(1,2,4)-triazolyl-2-p-chlorophenylpropan-2-ol (Compound No.1 of Table I)

Stage 1

A Grignard reagent [prepared from p-chloroiodobenzene (0.22 mol) in sodium-dried diethyl ether (65 ml) and magnesium turnings (0.24 g atoms)] was added dropwise over 1 hour to a stirred solution of 1,3-dichloroacetone (0.2 mol) in sodium-dried diethyl ether (270 ml) maintained at −60° C. The mixture was stirred for a further 1 hour at −60° after complete addition. Glacial acetic acid (21 ml) in diethyl ether (320 ml) was added dropwise to the solution and the temperature allowed to rise to 0° C. The solution was washed with water (2×150 ml) and dried (Na$_2$SO$_4$). Removal of the solvent gave a pale yellow oil which was distilled at the oil pump to give 1,3-dichloro-2-p-chlorophenyl-propan-2-ol (85%), b.p. 100°-2°/0.2 mmHg.

Stage 2

1,2,4-triazole (0.045 mol) was added portionwise to a stirred suspension of sodium hydride (0.045 mol—using 50% suspension in oil) in dimethyl formamide (15 ml) and stirring was continued until the effervesence ceased. 1,3-Dichloro-2-p-chlorophenyl-propan-2-ol (0.015 mol) in dimethylformamide (5 ml) was added dropwise to the solution at 20° and stirring was continued at 100° for 6 hours. After cooling to room temperature, the mixture was poured into water and the solid formed was filtered off and washed with diethyl ether. Recrystallization from ethyl acetate gave the title compound as a crystalline solid (50% yield), m.p. 153°–155° C.

The remaining compounds in Table I, that is compounds Nos. 3 to 32 were similarly prepared in Examples 1 and 2 using the appropriate starting substances. Details of crystallisation and other purification techniques are as follows:

| COMPOUND NO | RECRYSTALLISATION DETAILS AND COMMENTS ON PREPARATION |
|---|---|
| 1 | From ethyl acetate |
| 2 | From ethyl acetate: ether after chromatography on silica |
| 3 | From ethyl acetate: 60–80 petrol after chromatography on silica |
| 4 | From ethyl acetate after chromatography on silica |
| 5 | From chromatography on silica |
| 6 | From ethyl acetate after chromatography on silica |
| 7 | From chromatography on silica |
| 8 | Imidazole used in place of triazole in Stage 2. Chromatographed on alumina. Recrystallised from methanol/ethyl acetate as oxalate salt. |
| 9 | Crude solid triturated with ether. Recrystallised from ethyl acetate. |

EXAMPLE 2

This Example illustrates the preparation of the compound 1,3-Bis-(1,2,4)-triazolyl-2-(2,4-dichlorophenyl)-propan-ol--ol (Compound No.4 of Table I)

Stage 1

A Grignard reagent-(prepared by addition of 30 g 2,4-dichloroiodobenzene (0.11 mole) to 3.0 g magnesium turnings (0.125 g atoms) in refluxing ether (200 ml total) over 3 hours) was added dropwise to 12.7 g, 1,3-dichloroacetone (0.10 mole)—stirred in 100 ml dry ether in a Dry Ice-Acetone bath—over 45 minutes. The reaction was stirred for a further 4 hours allowing the cooling bath to warm to ca. 0° and 10 ml acetic acid in 100 ml ether added over 5 minutes.

Diluted with 400 ml water and the ethereal layer separated and washed successively with potassium metabisulphite solution (ca. 10%), water and saturated brine. Filtration through anhydrous sodium sulphate and evaporation in vacuo yielded 27.2 of a pale brown oil. This crude mixture of 1,3-dichloro-2-(2,4-dichlorophenyl)-propan-2-ol and 1,2-epoxy-3-chloro-2-(2,4-dichlorophenyl)-propane was used directly in the next stage.

Stage 2

Sodium hydride (50% dispersion in oil) 14.4 g (0.3 mole) was washed with 60–80 petrol twice, suspended in 50 ml dry DMF under argon and 1,2,4-triazole 21 g (0.30 moles) in 60 ml DMF added over 30 minutes at ≦50° C. When H$_2$ evolution had ceased (ca. 30 minutes after the addition) the crude dichloride/epoxide mixture from above, 27.2 g total, was added in 25 ml DMF including washings over 10 minutes at 25°–35° C. with stirring. After the addition the reaction mixture was heated with stirring for 6 hours at 100° C. It was then stirred overnight at room temperature, and the majority of the DMF evaporated in vacuo at ca. 50°–80°.

The dark residue was partitioned between 200 ml water and 200 ml chloroform. The aqueous portion was re-extracted with chloroform (2×100 ml) and the combined extracts washed with 100 ml water and 100 ml brine. Filtration through anhydrous sodium sulphate and evaporation in vacuo gave 20.5 g moist brown solid. Trituration with 200 ml boiling ether and filtration (cold) gave 10.2 g, 1,3-bis-(1,2,4)-triazolyl-2-(2,4-dichlorophenyl)-propan-2-ol as a pale tan solid m.p. 182°–185° C., pure by H. c. (silica gel K60; ethyl acetate: methanol, 4:1). The mother liquors from the triturations on chromatography on silica gel in CH$_2$Cl$_2$, and development with ethyl acetate followed by methanol-/ethyl acetate (1:4), yielded a further 0.90 g material of the same purity. Total yield 33% (based on DCA).

Anal: Calcdl. for C$_{13}$H$_{12}$Cl$_2$N$_6$O (339): C, 46.0; H, 3.50; N, 24.8. Found: C, 45.9; H, 3.6; N, 24.7.

P.m.r. CDCl$_3$ (90 MH$_3$) δ4.83 (q,4H, CH$_2$N), 5.64 (s, 1H,OH), 7.31 (m(ABX), 3H, Ar), 7.83 (s, 2H, Tr), 8.07 (s,2H,Tr) ppm.

EXAMPLE 3

This Example illustrates the preparation of the compound 1,3-Bis-(1,2,4)-triazolyl-2-n-butyl-propan-2-ol (Example No. 14 of Table I)

Stage I

The Grignard reagent [prepared from n-butylbromide (0.08 mol) in sodium-dried ether (50 ml) and magnesium turnings (0.08 g atoms)] was added dropwise over 1 hour to a stirred solution of 1,3-dichloroacetone (0.08 mol) in sodium-dried diethyl ether (100 ml) maintained at −60°. The mixture was stirred for a further 1 hour at −60° after complete addition. Glacial acetic acid (10 ml) was added dropwise and the temperature allowed to rise to 0°. The solution was washed with water (2×150 ml), and dried over anhydrous sodium sulphate. Removal of the solvent gave a pale red liquid which was distilled at the oil pump to give 1,3-dichloro-2-n-butyl-propan-2-ol (30%) b.p. 44°/0.04 mm Hg.

Stage 2

1,2,4-Triazole (0.067 mol) was added portionwise to a stirred suspension of sodium hydride (0.067 mol—using a 50% suspension in oil) in dimethyl formamide (30 ml) and stirring continued until the effervescence ceased. 1,3-Dichloro-2-n-butyl-propan-2-ol (0.022 mol) in dimethyl formamide (5 ml) was added dropwise to the solution at 20° and stirring continued at room temperature for 24 hours. The mixture was poured into water and the solid formed was filtered off and dried. Recrystallisation from ethyl acetate gave the title compound (30%) m.p. 61°–62° C.

EXAMPLE 4

This Example illustrates the preparation of the compound 2-(2,4-dichlorophenyl)-1-(imidazol-1-yl)-3-(1,2,4-triazol-1-yl)-2-propanol (compound No.13 of Table I)

Sodium hydride (50% suspension in oil—2.23 g) was suspended in dimethylformamide (30 ml) under an atmosphere of argon, and cooled in a water bath while imidazole (3.2 g) was added in portions. A solution of 2-(2,4-dichlorophenyl)-2-(1,2,4-triazol-1-ylmethyl)oxirane (6.4 g) in dimethylformamide (30 ml) was added, and the mixture was heated at 80° C. for 2 hours. The mixture was cooled, poured into water (200 ml) and extracted with methylene dichloride. The organic extract was washed with water twice and with brine twice, dried over sodium sulphate and filtered. The solvent was evaporated under reduced pressure, and the residue was chromatographed on a K60 silica column, eluting with 0 to 7% of methanol in methylene dichloride, to give 2-(2,4-dichlorophenyl)-1-(imidazol-1-yl)-3-(1,2,4-triazol-1-yl)-2-propanol, m.p. 169°–170° C.

The 2-(2,4-dichlorophenyl)-2-(1,2,4-triazol-1-ylmethyl)oxirane used as the starting material in the above process may be prepared as follows:

α-2,4-Trichloroacetophenone (20 g) was dissolved in acetonitrile (25 ml) and added dropwise to a refluxing solution of 1,2,4-triazole (6.2 g) and potassium carbonate (13.4 g) in acetonitrile (25 ml). When the addition was complete, the solution was allowed to cool and was stirred for 2 hours. The solvent was evaporated and the residue was partitioned between ethyl acetate and water. The ethyl acetate layer was separated, washed twice with water and twice with brine, dried over sodium sulphate and filtered. The filtrate was evaporated to dryness under reduced pressure, and the residue was chromatographed on a K60 silica column, eluting with ethyl acetate, to give 2,4-dichloro-α-(1,2,4-triazol-1-yl)acetophenone, which after crystallisation from ethyl acetate/60-80 petroleum ether, had m.p. 116°–117° C.

Sodium hydride (50% dispersion in oil—1.82 g) was washed three times with 40-60 petroleum ether, and trimethylsulphoxonium iodide (8.03 g) was added under an atmosphere of nitrogen, followed by dry dimethylsulphoxide (37 ml) dropwise. When the addition was complete, the mixture was stirred for 30 minutes then a solution of 2,4-dichloro-α-(1,2,4-triazol-1-yl)-acetophenone (8.5 g) in dimethylsulphoxide (25 ml) was added dropwise, and after the addition was complete, the reaction mixture was heated at 50° C. for 2 hours. The resulting solution was poured into water (200 ml) and extracted with methylene dichloride. The organic layer was separated, washed twice with brine, dried over sodium sulphate and filtered, and the filtrate was evaporated to dryness to give the required starting material, 2-(2,4-dichlorophenyl)-2-(1,2,4-triazol-1-yl)oxirane as a red oil, which was used in the above process without further purification.

The reaction scheme is:

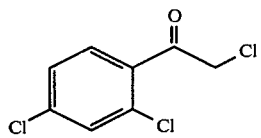  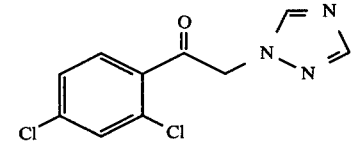

-continued

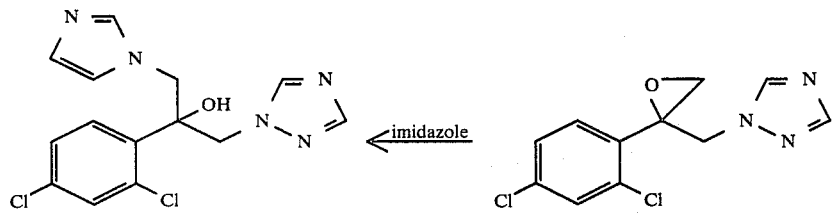

EXAMPLE 5

An emulsifiable concentrate was made up by mixing the ingredients, and stirring the mixture until all the constituents were dissolved.
Compound of Example 1: 10%
Ethylene dichloride: 40%
Calcium dodecylbenzenesulphate: 5%
"Lubrol" L: 10%
"Aromasol" H: 35%

EXAMPLE 6

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44-100, to obtain the desired size of grains.
Compound of Example 2: 50%
"Dispersol" T: 25%
"Lubrol" APN5: 1.5%
Sodium acetate: 23.5%

EXAMPLE 7

The ingredients were all ground together to produce a powder formulation readily dispersible in liquids.
Compound of Example 3: 45%
"Dispersol" T: 5%
"Lissapol" NX: 0.5%
"Cellofas" B600: 2%
Sodium acetate: 47.5%

EXAMPLE 8

The active ingredient was dissolved in a solvent and the resultant liquid was sprayed on to the granules of China clay. The solvent was then allowed to evaporate to produce a granular composition.
Compound of Example 4: 5%
China clay granules: 95%

EXAMPLE 9

A composition suitable for use as a seed dressing was prepared by mixing the three ingredients.
Compound of Example 1: 50%
Mineral oil: 2%
China clay: 48%

EXAMPLE 10

A dusting powder was prepared by mixing the active ingredient with talc.
Compound of Example 2: 5%
Talc: 95%

EXAMPLE 11

A Col formulation was prepared by ball-milling the constituents set out below and then forming an aqueous suspension of the ground mixture with water.
Compound of Example 3: 40% P1 "Dispersol" T: 10%
"Lubrol" APN5: 1%
Water:

EXAMPLE 12

A dispersible powder formulation was made by mixing together the ingredients set out below and then grinding the mixture until all were thoroughly mixed.
Compound of Example 4: 25%
"Aerosol" OT/B: 2%
"Dispersol" A.C.: 5%
China clay: 28%
Silica: 40%

EXAMPLE 13

This Example illustrates the preparation of a dispersible powder formulation. The ingredients were mixed and the mixture then ground in a comminution mill.
Compound of Example 1: 25%
"Perminal" BX: 1%
"Dispersol" T: 5%
Polyvinylpyrrolidone: 10%
Silica: 25%
China clay: 34%

EXAMPLE 14

The ingredients set out below were formulated into a dispersible powder by mixing then grinding the ingredients.
Compound of Example 2: 25%
"Aerosol" OT/B: 2%
"Dispersol" A: 5%
China clay: 68%

In Examples 5 to 14 the proportions of the ingredients given are by weight.

There now follows an explanation of the compositions or substances represented by the various Trade Marks and Trade Names mentioned above.
LUBROL L: a condensate of nonyl phenol 1 mole) with ethylene oxide (13 moles)
AROMASOL H: a solvent mixture of alkylbenzenes
DISPERSOL T & AC: a mixture of sodium sulphate and a condensate of formaldehyde with sodium naphthalene sulphonate
LUBROL APN5: a condensate of nonyl phenol (1 mole) with naphthalene oxide (5.5 moles)
CELLOFAS B600: a sodium carboxymethyl cellulose thickener
LISSAPOL NX: a condensate of nonyl phenol (1 mole) with ethylene oxide (8 moles)
AEROSOL OR/B: dioctyl sodium sulphosuccinate PERMINAL BX: a sodium alkyl naphthalene sulphonate

EXAMPLE 15

The compounds were tested against a variety of foliar fungal diseases of plants. The technique employed was as follows.

The plants were grown in John Innes Potting Compost (No 1 or 2) in 4 cm diameter minipots. A layer of fine sand was placed at the bottom of the pots containing the dicotyledonous plants to facilitate uptake of test compound by the roots. The test compounds were formulated either by bead milling with aqueous Dispersol T or as a solution in acetone or acetone/ethanol which was diluted to the required concentration immediately before use. For the foliage diseases, suspensions (100 ppm active ingredient) were sprayed on to the soil. Exceptions to this were the tests on *Botrytis cinerea*, *Plasmopara viticola* and *Venturia inaequalis*. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the diseases. An exception was the test on Erysiphe graminis in which the plants were inoculated 24 hours before treatment. After inoculation, the plants were put into an appropriate environment to allow infection to take plate and then incubated until the disease was ready for assessment. The period between inoculation and assessment varied from four to fourteen days according to the disease and environment.

The disease control was recorded by the following grading:
4 = no disease
3 = trace—5% of disease on untreated plants
2 = 6–25% of disease on untreated plants
1 = 26–59% of disease on untreated plants
0 = 60–100% of disease on untreated plants
The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | BOTRYTIS CINEREA (TOMATO) | CERCOSPORA ARACHIDICOLA (PEANUT) | VENTURIA INAEQUALIS (APPLE) |
|---|---|---|---|---|---|---|
| 1 | 3 | 4 | 0 | 3 | 4 | 4 |
| 2 | 3 | 4 | 2 | 1 | 4 | 4 |
| 3 | 4 | 4 | 0 | 0 | 4 | 4 |
| 4 | 4 | 4 |   | 3 | 4 | 4 |

EXAMPLE 16

This Example illustrates the plant growth regulating properties of the compounds. The compounds were applied in the form of a 4000 ppm solution in distilled water and the solution was then applied to the foliage of young seedlings of various plants. The experiments were replicated twice. After 12 or 13 days from treatment the plants were assessed for plant growth regulating effects and phytotoxic symptoms.

Table III shows the stunting effect of the compounds on the vegetative growth using the following grading:
1 = 0–30% retardation
2 = 31–75% retardation
3 = 75% retardation If no figure is given, the compound was substantially inactive as a stunting agent. Additional plant growth regulating properties are indicated as follows:
G = darker green leaf colour
A = apical effect
T = tillering effect

TABLE III

| COMPOUND NUMBER | SOYA COTTON | BEET | SUGAR TENUIS | *AGROSTIS XURIS* | *CYANO-GLOMERATA* | *DACTYLIS* WHEAT | LETTUCE | MAIZE | TOMATO |
|---|---|---|---|---|---|---|---|---|---|
| 1 | 3 |   | 1G |   | 1 |   |   | 2G | 2G |
| 4 | 1 | 1 | 1G | 2 | 1G | 1G | 1 | 2A | 1G | 3GA |

EXAMPLE 17

A mixture of 5, 10, 25, 50, 100 or 250 parts of compound no. 4 of Table I with 70 parts of calcium carbonate and 200 parts of a 10% maize starch past is dried and then passed through a 16 mesh screen. 5 parts of magnesium stearate are added and the granules are compressed to give a range of tablets suitable for oral administration for therapeutic purposes.

This active ingredient may be replaced by a therapeutically equivalent amount of any other triazole derivatives as hereinbefore defined.

EXAMPLE 18

A mixture of 2, 5, 10, 25, 50 or 100 parts of compound no. 4 of Table I, 500 parts of lactose and 100 parts of maize starch is treated with sufficient 10% maize starch paste to give a granular mass. Each mixture is passed through a 16-mesh screen, dried, mixed with 8 parts of magnesium stearate and compressed into tablets, thus giving a range of tablets suitable for oral administration for therapeutic purposes.

The active ingredient may be replaced by a therapeutically equivalent amount of any other triazole derivatives as hereinbefore defined.

EXAMPLE 19

A mixture of 100 parts of compound no. 4 of Table I and 190 parts of wheat germ oil is filled into soft gelatin capsules, to give capsules suitable for oral administration for therapeutic purposes.

The active ingredient may be replaced by a therapeutically equivalent amount of any other triazole derivative as hereinbefore defined.

EXAMPLE 20

A solution of 10 parts of compound no. 4 of Table I in 83 parts of water, 250 parts of glycerol and 125 parts of ethyl alcohol is mixed with a solution of 300 parts of sucrose in 150 parts of water. A suitable flavouring agent and colouring matter are then added to produce a syrup suitable for oral administration for therapeutic purposes.

The active ingredient may be replaced by a therapeutically equivalent amount of any other triazole derivative as hereinbefore defined.

EXAMPLE 21

A mixture of 3 parts of gum acacia and 1.5 parts of gum tragacanth is added to a mixture of 1 part of compound no. 4 of Table I and 33.7 parts of liquid paraffin. To the thoroughly triturated mixture is added slowly with stirring a solution of 0.1 part of cetyl alcohol-polyoxyethylene condensate, 40 parts of sucrose, 0.03 part of propyl p-hydroxybenzoate, 0.3 part of methyl p-hydroxybenzoate, a suitable flavouring agent and 0.002 part of edible dyestuff in 110 parts of water. The mixture is then homogenized in conventional manner known in the art to produce an emulsion suitable for oral administration for therapeutic purposes.

The active ingredient may be replaced by a therapeutically equivalent amount of any other triazole derivative as hereinbefore defined.

EXAMPLE 22

A mixture of 0.5 part of finely divided compound no. 4 of Table I propionamide in 3 parts of propylene glycol and 2 parts of ethylene glycol monoether was added to a stirred mixture of 4 parts of lanolin and 90.5 parts of molten soft white paraffin. The resulting mixture was allowed to cool to room temperature with rapid stirring, to give a uniform ointment containing 0.5% by weight of active ingredient suitable for topical administration for therapeutic purposes.

The active ingredient may be replaced by another triazole derivative as hereinbefore defined to give similar ointments.

EXAMPLE 23

A solution was prepared of 1 part of compound no. 4 of Table I in 20 parts of ethanol and 27 parts of diethylene glycol monoethyl ester, then 50 parts of purified water was added, followed by 2 parts of a carboxypolymethylene gelling agent ("Carbapol 940"—Trade Mark) to give a finely dispersed gel suitable for topical administration for therapeutic purposes.

The active ingredient may be replaced by any other triazole or imidazole compound, or derivative, as hereinbefore described.

EXAMPLE 24

This Example illustrates the preparation of the acetyl ester (that is the acetate) of the compound of Example 4 (Compound No 4 of Table I).

The reaction was as follows:

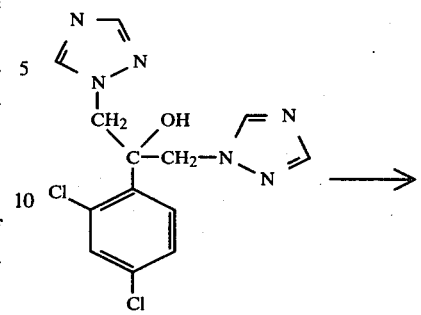

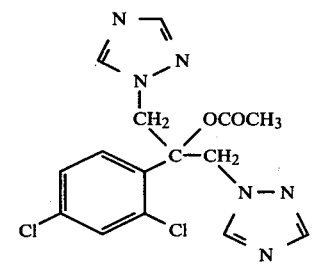

The compound of Example 4 (Compound No 4 of Table I) 1.70 g (5 m.mole) was heated on the steam bath for 7 hours in 40 ml acetic anhydride containing 100 mg 4-dimethylaminopyridine. The reaction mixture was evaporated in vacuo to give an orange gum. This was dried under vacuum overnight and dissolved in hot ethyl acetate/ether and cooled to give 840 mg. of a pale tan solid m.p. 176°–179° C. Pure by T.l.c. on silica gel (ethyl acetate/methanol 9:1).

Anal: C 47.24/3.70/22.0,$C_{15}H_{14}Cl_2N_6O_2$ (381): F 47.7/3.8/21.3.

PMR-DMSO-$d_6$ 90 MHz$\delta$2.04 (s,3H,$CH_3CO$) 5.17 (q, 4H, $\underline{CH_2}$N), 7.20/7.23 (q/d,2H,Ar), 7.60 (d, 1H, Ar), 7.97/8.33 (s/s, 2H each, Tr) -ppm.

EXAMPLE 25

This example illustrates the preparation of the 2,6-dichlorobenzyl ether of the Compound of Example 1 (Compound No 1 of Table I). The reaction was as follows:

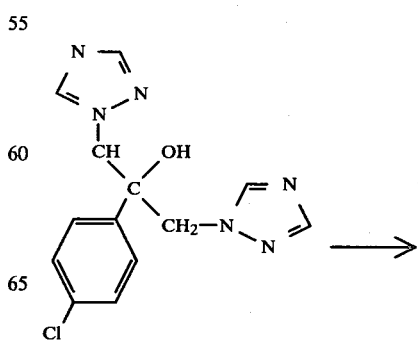

-continued

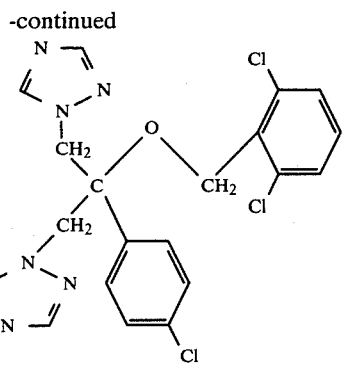

The compound of Example 1 (Compound No 1 of Table I), 3.04 g (10 m.mole) was added in portions to 0.50 g of 50% NaH dispersion in oil (washed free of oil with 60–80 petrol) at 20°–35° in 15 ml DMF. After $H_2$ evolution had ceased, 2.0 g 2,6-dichlorobenzyl chloride (10 m.mole) in 20 ml DMF was added and the reaction mixture was stirred at 90°–100° for 48 hours. It was then partitioned between ethyl acetate and water and the organic layer separated and washed three times with water and once with brine. Drying with anhydrous $Na_2SO_4$ and evaporation in vacuo gave 4.40 g of a pale yellow oil. After cooling in ether/ethyl acetate 1.2 g of a tarry solid and 1.35 g of a pale yellow solid (second crop) were obtained and the first crop has m.p. 133°–139°. Recrystallisation of the combined crops gave 2.20 g of near colourless plates, m.p. 133°–138° C. Pure by T.l.c. on silica gel (ethyl acetate/$CH_3OH$; 9:1).

Anal: C 48.0/4.2/16.8 for $C_{20}H_{17}Cl_3N_6O$ $2H_2O$ (463.5; 36): F 47.7/3.9/16.7.

P.m.r. $CDCL_3$-DMSO-$d_6$ (90 MH$_Z$) δ3.21 s,$H_2O$), 4.90 (s, 2H,$CH_2O$), 4.97 (s,4H,$C\underline{H}_2N$), 7.30 (m,7H,Ar), 7.80/8.15 (s/s, 2H each, Tr). ppm.

I claim:

1. A compound selected from the group consisting of compounds having the formula:

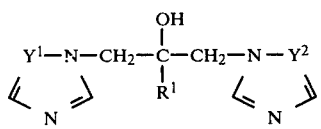

wherein $R^1$ is selected from the group consisting of: phenyl or benzyl substituted with one or more of the following: halogen, alkyl or haloalkyl each containing from 1 to 5 carbon atoms, alkoxy or haloalkoxy each containing from 1 to 4 carbon atoms, nitro, cyano, hydroxy, alkylthio containing from 1 to 40 carbon atoms, vinyl, phenyl or phenoxy; and wherein the alkyl moiety of the benzyl is unsubstituted, or substituted with alkyl containing from 1 to 4 carbon atoms, phenyl or chlorophenyl, $Y^1$ and $Y^2$ are =CH— or =N—; and salts, metal complexes, methyl, ethyl, propyl, butyl, phenyl, benzyl, p-chlorobenzyl, allyl and propargyl ethers and acetate, pivaloate, benzoate, tosylate and mesylate esters thereof.

2. A compound according to claim 1 wherein the phenyl or benzyl is unsubstituted, or substituted with one, two or three of the following: halogen, methyl, methoxy, trifluoromethyl, trifluoromethoxy, phenyl, halophenyl, phenoxy or vinyl groups; and wherein the alkyl moiety of the benzyl is unsubstituted or substituted with methyl, ethyl or phenyl.

3. 1,3-Bis-(1,2,4)-triazolyl-2-(2,4-dichlorphenyl)-propan-2-ol having the structure:

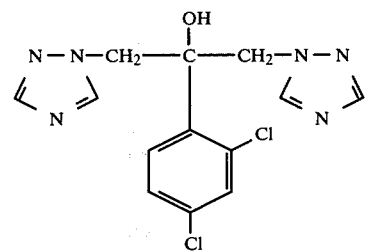

4. A pharmaceutical or veterinary fungicidal composition which comprises an effective amount of a compound according to claim 1 together with a pharmaceutically or veterinary-acceptable diluent or carrier.

5. A composition for combating fungi, or for regulating plant growth, which comprises, as an active ingredient, an effective amount of a compound as defined in claim 1.

6. A process for combating fungi, or regulating plant growth, which comprises applying to a plant, to seed of a plant or to the locus of a plant or seed, an effective amount of a compound as defined in claim 1.

7. A method of treatment of candidiasis or human dermatophyte infections which comprises administering to a human or animal an effective amount of a compound as claimed in claim 1.

* * * * *